US009247763B2

(12) United States Patent
Bouritius et al.

(10) Patent No.: US 9,247,763 B2
(45) Date of Patent: Feb. 2, 2016

(54) CARBOHYDRATE FRACTION AND USE THEREOF FOR A FLAT POSTPRANDIAL GLUCOSE RESPONSE (75) Inventors: Houkje Bouritius, Zeist (NL); Evan Abrahamse, Amersfoort (NL); Wynette Hermina Agnes Kiers, Heteren (NL); Chantal Severijnen, Amersfoort (NL); Katrien Maria Jozefa van Laere, Heteren (NL); Robert Johan Joseph Hageman, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 1337 days.

(21) Appl. No.: 11/994,706

(22) PCT Filed: Jul. 5, 2006

(86) PCT No.: PCT/NL2006/050166
§ 371 (c)(1),
(2), (4) Date: Sep. 22, 2008

(87) PCT Pub. No.: WO2007/004883
PCT Pub. Date: Jan. 11, 2007

(65) Prior Publication Data
US 2009/0011990 A1  Jan. 8, 2009

(30) Foreign Application Priority Data
Jul. 5, 2005    (EP) .................................... 05106102
Dec. 20, 2005  (EP) .................................... 05112530

(51) Int. Cl.
A61K 31/718   (2006.01)
A61K 31/7016  (2006.01)
A23L 1/29     (2006.01)
A23L 1/308    (2006.01)
A23L 1/0522   (2006.01)
A23L 1/09     (2006.01)
A61K 31/7004  (2006.01)

(52) U.S. Cl.
CPC . A23L 1/296 (2013.01); A23L 1/09 (2013.01); A23L 1/095 (2013.01); A23L 1/3081 (2013.01); A61K 31/7004 (2013.01); A61K 31/718 (2013.01); A23V 2002/00 (2013.01)

(58) Field of Classification Search
None
See application file for complete search history.

(56) References Cited

U.S. PATENT DOCUMENTS

| 5,468,734 | A | * | 11/1995 | Seri et al. ......................... 514/23 |
| 5,605,893 | A | * | 2/1997 | Kaufman ................. A21D 2/16 424/439 |
| 5,776,887 | A | * | 7/1998 | Wibert et al. ..................... 514/5.5 |
| 5,792,754 | A | * | 8/1998 | Green et al. ..................... 514/60 |
| 5,843,921 | A | * | 12/1998 | Kaufman ................. A21D 2/16 424/439 |
| 6,534,487 | B1 | * | 3/2003 | Kaufman ............... A23L 1/0522 424/439 |
| 6,893,627 | B2 | | 5/2005 | Ribnicky et al. |
| 7,037,531 | B2 | | 5/2006 | King et al. |
| 2002/0094971 | A1 | * | 7/2002 | Hansson et al. ................ 514/60 |
| 2003/0072822 | A1 | | 4/2003 | Ribnicky et al. |
| 2003/0147939 | A1 | | 8/2003 | King et al. |
| 2004/0086615 | A1 | * | 5/2004 | Johnson et al. ............... 426/548 |
| 2006/0008574 | A1 | | 1/2006 | Begli et al. |

FOREIGN PATENT DOCUMENTS

| EP | 1 088 832 A1 | 4/2001 |
| EP | 0 846 704 B1 | 3/2002 |
| EP | 1 491 557 A1 | 12/2004 |
| WO | WO-03/079818 A1 | 10/2003 |
| WO | WO-03/104473 A2 | 12/2003 |

OTHER PUBLICATIONS

Ercan, N., et al. "Effects of glucose, galactose, and lactose ingestion on the plasma glucose and insulin response in persons with non-insulin-dependent diabetes mellitus." Metabolism 42.12 (1993): 1560-1567.*
H. N. Englyst et al., "Classifications and measurements of nutritionally important starch fractions", European Journal of Clinical Nutrition (1992) 46 (Suppl 2) S33-S50.
G. Annison et al., "Nutritional Role of Resistant Starch: Chemical Structure vs Physiological Function", Annu. Rev. Nutr. 1994, 14:297-320.
Klaus N. Englyst et al., "Rapidly available glucose in foods: an in vitro measurement that relfects the glycemic response", Am .J. Clin. Nutr. 1999;69:448-454.
Tomoyuki Mishima et al., "Studies on Absorption and Hydrolysis of Ethyl α-D-Glucoside in Rat Intestine", J. Agric. Food Chem., 53(18), 2005. Abstract.

(Continued)

Primary Examiner — Bethany Barham
Assistant Examiner — Peter Anthopolos
(74) Attorney, Agent, or Firm — Sunit Talapatra; Foley & Lardner LLP (57) ABSTRACT The invention relates to a combination of heat-treated nutritional composition having a carbohydrate fraction comprising a) 5-30 wt % of one or more monosaccharides selected from galactose, ribose and mannose; b) carbohydrates capable of providing b1) sustained release glucose and b2) rapidly available glucose; c) optionally fructose; d) glucose-containing disaccharides other than maltose and sucrose; and e) optionally sugar polyols. The invention also pertains to the use of such a heat-treated nutritional composition for controlling glucose levels in blood and/or tissue, especially for preventing and/or treating diabetics, insulin-resistance, obesity, postprandial glucose response, metabolic syndrome, syndrome X, hyperglycemia, hypertriglyceridemia, hyperinsulinemia, dyslipidemia, dysfibrinolysis and/or disorders associated with major surgery or trauma.

18 Claims, 3 Drawing Sheets (56) References Cited

OTHER PUBLICATIONS

Barry V. McCleary et al., "Measurement of Resistant Starch by Enzymatic Digestion in Starch and Selected Plant Materials: Collaborative Study", Journal of AOAC International, vol. 85, No. 5, 2002, pp. 1103-1111.

Sungsoo C. Lee et al., "Determination of Total, Soluble, and Insoluble Dietary Fiber in Foods—Enzymatic—Gravimetric Method, MES-TRIS Buffer: Collaborative Study", Journal of AOAC International, vol. 75, No. 3, 1992, pp. 395-416.

Leon Prosky, "Inulin and Oligofructose are Part of the Dietary Fiber Complex", Journal of AOAC International, vol. 82, No. 2, 1999, pp. 223-226.

Suk-Hun Yun et al., "Estimation of Amylose Content of Starches after Precipitation of Amylopectin by Concanavalin-A", Starch/Starke 42(1990) Nr. 8, S. 302-305.

William R. Morrison et al., "An Improved Colorimetric Procedure for Determining Apparent and Total Amylose in Cereal and Other Starches", Food Science Divisional Department of Bioscience and Technology, University of Strathclyde, Glasgow, G1 1SD, Scotland, UK, 1982, pp. 9-20.

International Search Report for PCT/NL2006/050166, dated Jan. 29, 2007, 3 pages.

Kishida et al., "Heat Moisture Treatament of High Amylose Cornstarch Increases its Resistant Starch Content but Not its Physiologic Effects in Rats," J. Nutr., vol. 131, No. 10, 2001, pp. 2716-2721 [XP002339752].

Reader et al., "Glycemic and Insulinemic Response of Subjects with Type 2 Diabetes after Consumption of Three Energy Bars," J. Am. Dietetic Assn., vol. 102, No. 8, Aug. 2002, pp. 1139-1142 [XP004908709].

\* cited by examiner

Figure 1

Glucose

Figure 2

Insulin

Figure 3

CARBOHYDRATE FRACTION AND USE THEREOF FOR A FLAT POSTPRANDIAL GLUCOSE RESPONSE

FIELD OF THE INVENTION

The invention relates to a carbohydrate fraction that gives a sustained and lower glucose release after consumption.

BACKGROUND OF THE INVENTION

Glucose is an important source of energy to the cells in the human body and abundantly present in food ingredients. After consumption of starch or other dietetic available sources of glucose and their subsequent digestion, glucose is released in the gastrointestinal tract, where it is rapidly and effectively absorbed from the intestinal lumen. This will usually increase glucose concentrations in blood. The change in glucose after consumption of a food is called the postprandial glucose response (PPGR), which can be measured as the area under the curve (AUC) which plots the plasma glucose concentration with time. The human body strives to maintain homeostasis of glucose levels in tissue and blood with time, in order to allow proper functioning of all cells. One important instrument to achieve glucose homeostasis is the release of insulin by the pancreas when the concentration of specific food components like glucose starts to increase. Under normal circumstances this will increase glucose transport into the cell and the formation of glycogen using glucose, and trigger other metabolic changes, therewith rapidly causing the blood glucose levels to decrease to normal levels.

A person that does not react properly on released insulin is said to be insulin-resistant. Large groups of persons suffer from insulin resistance like many obese persons, persons suffering from the so called metabolic syndrome (or syndrome X), diabetics and many patients in hospitals or nursing homes who developed a temporarily or longer lasting insulin resistance as a cause of their disease. Part of the diabetics also experience an insufficient capacity to increase insulin concentrations in blood after consumption of food (called postprandially). Persons that suffer from insulin-resistance demonstrate abnormal high postprandial glucose response, even after consumption of moderate amounts of food ingredients that comprise glucose. When high postprandial glucose concentrations occur relatively frequently and over longer periods of time, they can cause several severe health problems. Known secondary side effects, as can be found in diabetics, are problems in the cardiovascular system, such as hypertension, atherosclerosis, bad blood supply to peripheral tissues, stroke, heart attacks etc., as well as problems in the kidney, in particular an abnormal glomerular filtration rate, and a wide range of neuropathies and retinopathies like cataract. It was also found that mortality of severe disease in hospital patients is associated with the severity of insulin resistance.

The decrease of postprandial glucose response (PPGR) has been the subject of numerous research efforts. Many types of carbohydrates have been proposed to induce a low PPGR. Also inclusion of dietetic fibre in a nutritional product has been proposed for this purpose, for example viscous fibres, like gums or pectin. The disadvantage of using such fibres is the increase in viscosity when used in liquid products in amounts that are effective. According to the European FLAIR Concerted Action on Resistant Starch (EURESTA) resistant starch is defined as "the sum of starch and products of starch hydrolysis not absorbed in the small intestine of healthy individuals".

Commercially available ingredients that can be used as a source of resistant starch are mainly considered to be a source of fibre, so being non-digestible, thereby neglecting the value of the remaining digestible part of the ingredient as a principle source of digestible carbohydrates. It is generally avoided to include fibres in Western nutritional food products in amounts larger than 20-40 grams per daily dose, as they are believed to cause gastrointestinal discomfort in these doses, like bloating, flatulence and loss of appetite. Patients in hospitals or nursing homes may also develop constipation or a high faecal mass when too high amounts or the wrong type of fibres are consumed, especially in combination with drinking too little. In liquid enteral nutrition for the latter group of patients typically about 1 g fibres is included in a nutritional product per 20 g digestible carbohydrates.

Englyst H. N. et al., *Eur. J. Clin. Nutr.*, 46, Suppl. 2, S33-S50 (1992), classify resistant starch (RS) into three categories for reasons of different digestion resistance: Type 1 RS are starches which are physically inaccessible to the digestive enzymes, type 2 RS are starches that exist as granules and can comprise predominantly amylose, and type 3 RS are retrograded starches. Cross-linked and/or chemically modified starches are sometimes considered to be type 4 RS, but their non-food grade status makes them at present undesirable for commercial application in the food industry.

Each of these ingredients can be manufactured differently and their behaviour in vivo depends on the way the ingredient was processed, prior to consumption. Typically manufacturers of resistant starch ingredients develop an ingredient having a RS level that is as high as possible and this amount must be constant and independent of the way of processing of the ingredient when it is included in new food products.

It is known that the digestibility of native starch can change during food processing, especially when heat is applied to the food carbohydrates. Heat treatment plays an important role in manufacturing of clinical liquid formulae, in order to kill micro-organisms or spores thereof and thereby make the formulae safe for consumption by persons that suffer from disease or health disorders or persons who are immune-compromised and/or to prevent spoilage of the formulae during shelf life. A heat treatment may have different effects on the starch properties, as does moisture content, pressure, pH, ionic strength, during processing and in the nutritional product. Annison G. and Topping D. L., *Ann. Rev. Nutr.* 1994, 14, 297-320, show a significant increase of the viscosity of a starch-containing nutrition when subjected to a specific heat treatment, and even gelatinization may occur, which is undesirable in liquid clinical nutritional products that are intended to be used for tube—or sip-feeding. In addition, the starches may crystallize and precipitate in production lines or in the product, therewith causing problems with homogeneity and blockage of tubing lines. Starch crystals may cause a sandy feeling in the mouth, when consumed.

In the art little attention is paid to the fraction of resistant starch ingredients that is actually available in vivo to man. Most commercially available RS ingredients are to a varying degree partially digestible within 20 minutes after consumption. The remainder is undigested by the enzymes that are released within the human gastrointestinal tract and used as fermentable substrate by colonic micro-organisms. Therefore such resistant starch ingredients do not behave as sustained release carbohydrates.

For example, EP-A-1.088.832 discloses a granular starch that is prepared by selected heat-moisture treatment and which heat-treated starch is made resistant for more than 80%, preferably has a molecular weight of 5-20 kDa (degree of polymerization (DP) of 30-123) and a low amylopectin content. The material is appreciated as source of dietary fibre. Food products are described which comprise more than 20 wt % of total dietary fibre. EP-A-0846704 describes a retrograded starch having more than 55% resistant starch with more than 50% of linear chains of α-glucans having a DP between 10-35 and a DSC melting peak temperature below 115° C. It is suitable for use as a prebiotic component, in particular as a butyrate-producing fibre.

A starch having sustained digestion properties is taught in US 2003/0219520. The enzymatically debranched starch comprises at least 90% linear α-glucans, preferably a highly crystalline amylose having 6-65 anhydro-glucose units linked by α-1,4-D-glucoside bonds and a DE>6.0. No change in the material properties is observed during typical food processing conditions, when included in an amount of 1-50 wt % in a wide range of food products. Upon consumption, between 22 and 50 wt % is digested in the first twenty minutes, and 48-74 wt % is digested within two hours, after start of the test. Table 2 demonstrates the digestibility profile after a specific heat treatment at high or low moisture results: about 31-40% is digested during the first 20 minutes and 65-70% during the first 120 minutes after start of their test. The document is silent about the behaviour of the ingredient, when it is subjected to heating at higher temperatures and in particular ultra high heat treatments, as can be beneficially used during manufacture of enteral clinical nutrition. It is also silent about the effect of heating in a matrix that comprises proteins and/or lipids and/or other carbohydrate fractions. These components are known to be able to interact with amylose crystallization and therewith digestibility.

It is therefore an object of the invention to provide a nutritional product that is heat-treated and safe with regard to the presence of micro organisms, spores and other potentially harmful components, that is attractive to the consumer from an organoleptic point of view, especially in terms of mouth feel of the product when it is stored for prolonged times, and that is extremely effective in providing rapidly glucose to the consumer and maintaining a clinically significant supply of glucose during a prolonged time without resulting in undesirably high concentrations of glucose in the blood, even in persons that have become insulin resistant.

It is a further object of the invention to provide such products to persons that suffer from insulin resistance in order to prevent development of disorders which result from prolonged and frequent high levels of glucose in blood, such as those diseases that result from advanced glycation products (AGE), neuropathies, retina problems, and kidney problems.

DESCRIPTION OF THE INVENTION

It is now found that the combination of specific types of slowly digestible starches and one or more of the monosaccharides galactose, mannose and ribose is suitable for providing glucose to the human body in a slow released and sustained way, wherein the monosaccharides contribute to the glucose availability through metabolic conversion. Not only does this combination have a positive effect on the glycemic and insulinemic response (GI) or the total area under the PPGR curve, but it also establishes a substantially flat PPGR over longer times. A desirable PPGR is found to be one that shows a rapid but limited initial increase of the concentration of glucose in blood after administration, in order to give a quick improvement of energy status and prevent too low levels of glucose for proper functioning, and then stabilizes for longer times. This is particularly important for persons suffering from hypoglycemic levels, which are defined to be fasting glucose levels below 3.0 mM. The slowly digestible starch provides sustained glucose release between 20 minutes and two hours after consumption, whereas the abovementioned non-glucose monosaccharides function as an insulin-releasing agent to stimulate the uptake of the blood glucose, and moreover, to decrease the amount of metabolic stress the liver experiences. The prolonged increase of plasma glucose levels is especially important for persons that cannot eat at regular intervals and for example as night time formula for infants.

It is therefore an object of the invention to provide a nutritional composition that is safe for consumption by those persons that may benefit from consuming a rapidly available and sustained release glucose source and that comprises fats, proteins and digestible carbohydrates, and wherein the digestible carbohydrate fraction comprises galactose, mannose and/or ribose, a sustained release glucose source, and a rapidly available glucose source.

Particularly, the invention relates to a heat-treated nutritional composition comprising lipids, proteins and carbohydrates, wherein the carbohydrate fraction comprises a) one or more monosaccharides selected from galactose, ribose and mannose; b) carbohydrates capable of providing b1) sustained release glucose and optionally b2) rapidly available glucose; c) optionally fructose; d) optionally glucose-containing disaccharides other than maltose and sucrose; and e) optionally sugar polyols, wherein the heat-treated nutritional composition comprises 5-30 wt % of group a) and wherein group b) provides 30-65 wt % sustained release glucose and 15-40 wt % rapidly available glucose, based on the dry weight of the sum of groups a-e in the heat-treated nutritional composition. The product may be a dry product or, preferably, a non-viscous liquid product.

The invention further relates to a heat-treated nutritional composition comprising lipids, proteins and carbohydrates, wherein the carbohydrate fraction comprises a) one or more monosaccharides selected from galactose, ribose and mannose; b) carbohydrates capable of providing b1) sustained release glucose and b2) rapidly available glucose; c) optionally fructose; d) glucose-containing disaccharides other than maltose and sucrose; and e) optionally sugar polyols, wherein the heat-treated nutritional composition comprises 5-30 wt % of group a) and 5-30 wt % of group d), and wherein group b) provides 5-40 wt % b2) rapidly available glucose, based on the dry weight of the sum of groups a-e in the heat-treated nutritional composition.

The invention also pertains to the use of such heat-treated nutritional compositions for controlling glucose levels in blood and/or tissue in a mammal in need thereof, in particular for the prevention and/or treatment of diabetics, insulin-resistance, obesity, and controlling postprandial glucose response.

In particular, the digestible carbohydrate fraction provides 5-65 wt % of b1) glucose within 20-120 minutes after start of the digestion process as measured by the method described by Englyst et al, *Am. J. Clin. Nutr.* 1999, 69, 448-454. The amount of sustained release glucose source in the product is therefore the weight amount of glucose that becomes available between 20 and 120 minutes in this test. Typically the last precursor for glucose production in the Englyst test is either maltose or sucrose. Obviously, glucose supplied by metabolic conversion by the human body via galactose, mannose or ribose does not contribute to the availability of glucose according to the Englyst method, which stimulates digestion in the GI tract. Gluco-oligosaccharides which do not produce glucose according to the Englyst test (whether within 20 minute or longer), but which are hydrolysed in a rat intestinal hydrolysis test (see Mishima et al., *J. Agric. Food Chem.* 2005, 53, 7257-7261) are considered to be sustained release glucose sources.

In addition to those digestible carbohydrates according to the Englyst method, group b) also comprises oligosaccharides having a chain-length of 3 to 20 anhydromonose units, at least half of which are connected to each other via no n-α-1-4 bonds, e.g. by α-1,1, α-1,3, α-1,5 and α-1,6 bonds. Though these oligosaccharides release glucose in a sustained way in test systems which mimic intestinal digestion system in mammals, e.g. by using a mixture of intestinal enzymes which include brush border enzymes, the oligosaccharides will typically not produce a raise in plasma glucose levels after consumption thereof in amounts up to 25 grams bolus for an adult human being. Examples of such oligosaccharides are isomalto-oligosaccharides and other gluco-oligosaccharides obtained by transglucosylation of maltose, maltodextrins or other substrates, as described in WO04/081022, EP-A 1229803 and WO 05/089483. Certain oligosaccharides are also referred to as 'resistant maltodextrins'; the digestible part thereof is also covered by the sustained-release glucose sources of the invention The terms "rapidly digestible starch" (RDS), "slowly digestible starch" (SDS) and "non-digestible starch" (NDS) are obtained from the classification taught by Englyst, H. N. et al., *Eur. J. Clinical Nutrition* (1992) 46, S33-S50. The classification method involves incubation with pancreatic amylase and amyloglucosidase at 37° C. RDS is the starch hydrolysed during the first 20 minutes, and SDS is the starch hydrolysed in the following 100 minutes, i.e. between 20-120 minutes after the start of incubation. NDS is that fraction of the starch which escapes digestion during the first 120 minutes after start of the digestion test, NDS coinciding with the RS part of a resistant starch ingredient throughout the application. The contents of the relevant pages S35, S38 and S39 describing the classification method are hereby incorporated by reference. The total amount of starch TS, including resistant starch, is determined according to the method as provided by McCleary, *J Assoc. Off. Anal. Chem. Int*, 85, 1103-1111.

The term "rapidly available glucose" thus refers to the glucose that is available within 20 minutes according to the Englyst method, comprising both readily available glucose and glucose that only becomes available after digestion, but within 20 minutes, such as glucose obtained from RDS. The amounts of rapidly available glucose and sustained release glucose are calculated as the weight amount of available glucose provided by the source, relative to the weight of the digestible carbohydrate fraction. The total available glucose includes glucose released from the oligosaccharides having a chain-length of 3 to 20 anhydromonose units, at least half of which are connected to each other via non-α-1-4 bonds.

The digestible carbohydrate fraction comprises all carbohydrates that provide glucose according to the Englyst method, thus also including e.g. the glucose part of sucrose, and free glucose that is available without digestion, but also monosaccharides other than glucose that do not contribute according to the Englyst method, but which can be taken up by the body metabolically, especially galactose, ribose, mannose, fructose (including the fructose part of sucrose), and also glucose-containing disaccharides other than maltose and sucrose, as well as sugar alcohols, even if they are only partly or slowly digestible. The digestible carbohydrate part can include maltodextrins, glucose syrups. Thus, where "digestible carbohydrate fraction" is mentioned, it is meant the combination of monosaccharides selected from galactose, ribose and mannose, carbohydrates capable of providing sustained release glucose and rapidly available glucose according to the Englyst method, fructose, glucose-containing disaccharides other than maltose and sucrose, and sugar polyols, and also the aforementioned oligosaccharides having a chain-length of 3 to 20 anhydromonose units and non-α-1-4 bonds.

Thus, for the purpose of the invention, 'carbohydrates capable of providing sustained release glucose' include starch-type carbohydrates producing glucose within 20 and 120 minutes according to the Englyst test (see above), as well as glucose-containing oligosaccharides (typically non-α-1,4-linked, and excluding maltose and sucrose) producing glucose in the rat intestinal hydrolysis test of Mishima (see above).

Throughout the application the dry weight is determined as the constant value obtained upon drying with air at 100° C. at atmospheric pressure.

In the literature another distinction between digestible and non-digestible carbohydrates can be made on the basis of the method of Lee et al as published in *J. Assoc. Off. Anal. Chem.* 75: 395-416, 1992. According to their definition the non-digestible carbohydrates comprise resistant starch and optionally non-viscous fibres, like sufficiently far hydrolysed gums (Arabic, guar, gellan), hydrolysed pectin, hydrolysed tamarind or konjac, small β-glucans. If insulin, hydrolysed forms thereof and/or polyfructoses are present, the method of Prosky, *J. Assoc. Off. Anal. Chem.* 82: 223-226, 1999 is applied and added to the numbers obtained from Lee.

40-100%, preferably 60-90%, more preferably at least 75% of the sustained release glucose is provided by a resistant starch ingredient, i.e. a starch containing NDS and SDS.

The resistant starch ingredient comprises amylose (which are linear α-1,4 glucose-polysaccharides having at least 20 units), linear oligosaccharides and optionally amylopectin (branched polysaccharides). If present the amount of amylopectin should be 0-10, preferably 0-2 and more preferably 0-0.5 wt % of the digestible carbohydrates. The amount of amylopectin can be measured according to Yun et al, *Starch, Stärke* 42, 302-305 (1990) after defatting of the sample according to Morrison et al, *J Cereal Sci.*, 9-20, 1983. The resistant starch ingredient comprises 42-70 wt % and most preferably 45-60 wt % amylose, the remainder having less than 20 units.

The resistant starch ingredient comprises predominantly linear glucose polymers having a length of 10-2000 anhydroglucose units. About 35-70% and preferably 40-60% of the number of molecules have a degree of polymerization between 10 and 35. The remainder of the molecules contribute heavily to the mass of the material. Preferably between 40 and 60% of the mass of the ingredient has a degree of polymerization over 200 anhydro-glucose moieties.

After heat treatment the resistant starch ingredient comprises 5-80%, preferably 5-60%, preferably, 8-60%, more preferably 8-55%, most preferably 10-55% NDS. It comprises 5-55%, preferably 10-55%, more preferably 10-50%, more preferably 12-50, most preferably 12-40% SDS, and 10-70%, more preferably 15-60%, and most preferably 20-50% is RDS, the total of NDS, SDS and RDS being 100%. The resistant starch ingredient therefore contributes to the rapidly available glucose, slowly available glucose and indigestible carbohydrate fraction in the composition according the invention.

The total amount of rapidly available glucose sources in the nutritional composition is 5-40 wt %, more preferably 10-35 wt %, most preferably at least 20 wt %, and the sustained release glucose sources are present in an amount of 5-65 wt %, more preferably 10-60 wt %, most preferably 15-55 wt % of the digestible carbohydrate fraction. Alternatively, the total amount of rapidly available glucose sources in the nutritional composition is 15-40 wt %, more preferably 20-35 wt %, and the sustained release glucose sources are present in an amount of 30-65 wt %, more preferably 35-60 wt %, most preferably 40-55 wt % of the digestible carbohydrate fraction. The weight of these glucose sources are only taken into account for the parts that provide the rapidly available and sustained release glucose.

In the final product the amylose molecules may form crystals. If these are formed, the average particle size of the amylose crystals should preferably be less than 60, more preferably less than 40, and most preferably 5-20 micrometer. The amount of particles that has a particle size above 20 micron must be less than 50%, preferably less than 10, more preferably less than 5%. Such processing conditions are applied and those ingredients selected to ensure that during shelf life particle size of amylose crystals will not change outside the range as indicated.

The degree of polymerization DP of a molecule is determined by dividing its molecular weight by the molecular weight of 162 g/mol of the (anhydro)glucose unit. The digestible carbohydrate fraction of the invention preferably comprises a large fraction of sustained release glucose source. This source is preferably a starch and more preferably a resistant starch ingredient, i.e. starch having sustainedly digestible starch and only partial resistant starch properties. Such resistant starch ingredient is preferably present in an amount of 30-65, more preferably 35-60, most preferably 40-50 wt % of the digestible carbohydrate fraction, based on its contribution to the total amount of rapid and sustained release glucose.

The amount of resistant starch ingredient in the final liquid nutritional composition should be 0.5-10, preferably 0.8-8, more preferably 0.9-6 and most preferably 1-5 w/v %. This concentration is important to cause that the inclusion of the resistant starch ingredient in a liquid sterilized product results in the sustained release properties according to the invention.

The digestible carbohydrate fraction comprises galactose, mannose and/or ribose, preferably galactose and/or ribose, most preferably at least galactose. After absorption it can be slowly converted predominantly by liver transferases to glucose. The total amount of the monosaccharides galactose, ribose and mannose in the carbohydrate fraction must be 5-30, preferably 10-25 wt %, more preferably 15-22 wt % of the dry weight of the digestible carbohydrate fraction. In the context of the invention galactose and ribose also involve oxidized equivalents hereof, commonly referred to as aldaric acids, such as ribonic acid, ribaric acid, arabinaric acid. Equivalent dosages of alternative components can be calculated by using the same molar amount and correcting for the molecular weight of the alternative component.

The digestible carbohydrate fraction may comprise fructose as another monosaccharide different from glucose, but only in an amount below 10 wt % of the digestible carbohydrate fraction, preferably 1-10 wt %, more preferably less than 6 wt % and most preferably less than 4 wt %, in order to decrease the amount of metabolic stress which the liver must experience and to decrease the degree of Maillardation of the product. The contribution of fructose to the availability of glucose according to the Englyst method is zero. The amount of fructose includes the amount of fructose present in sucrose.

0-60%, preferably 10-55%, more preferably 20-50%, most preferably 25-50% of the rapidly available glucose is provided by a rapidly available glucose source other than the RDS fraction of the RS ingredient.

The digestible carbohydrate fraction can comprise glucose polymers other than the resistant starch ingredient, and which glucose polymers do not exhibit a SDS part. These non-SDS containing glucose polymers are defined to be those poly- and oligosaccharides having glucose as main constituent, e.g. more than 90 wt %, preferably more than 99 wt % consist of glucose moieties. They preferably contain less than 10 wt % RS. Typically these oligo- and polysaccharides have a MW of maximally 1,000,000 and preferably below 3200 and can be obtained by isolation and hydrolysis from plant material, like starches from corn, potato, cereals or tapioca. Many types of maltodextrins are suitable as well as glucose syrups and free glucose and other sources well known in the art of manufacturing enteral clinical nutrition and infant formulae. Maltodextrins having a dextrose equivalent value of 1-47 and preferably 2-40, more preferably 6-39 are preferred ingredients to provide rapid availability of glucose. Optionally the weight ratio of non-SDS-containing glucose polymer to the sum of the non-glucose monosaccharides galactose, mannose and ribose is 0.3-4, preferably 0.7-3 and more preferably 1.0-2.5.

The digestible carbohydrate fraction may also comprise free glucose. It has been found that the amount of free glucose and the amount of glucose syrup and glucose polymers, including the RDS part of the resistant starch ingredient exclusively contribute to the amount of rapidly available glucose.

It is preferred that the amount of rapidly available glucose is 1.25-10, more preferably 1.5-8 times the weight amount of free galactose, when galactose is included in the formula. When free ribose is included, the weight amount of rapidly available glucose, in particular of free glucose is 0.8-10 and preferably 1-8 times as high as the amount of free ribose. When free fructose is included, the ratio of the weight of rapidly available glucose to that of fructose should be in the range 1: 0-0.12.

The digestible carbohydrate fraction may comprise 5-30 wt %, preferably 5-20 wt. %, more preferably 10-20 wt. %, most preferably 10-15 wt. %, of a glucose-containing disaccharide other than maltose and sucrose, preferably a disaccharide selected from the group of lactose, palatinose, trehalose, leucrose and isomaltose, preferably lactose, palatinose and trehalose. It is preferred that the digestible carbohydrate fraction comprises a mixture of at least two of these disaccharides and more preferably a mixture of lactose and palatinose, except for persons who are extreme lactose-intolerant. Maltose and sucrose are excluded from this group of glucose-containing disaccharides, as they already contribute to the availability in the Englyst method for their glucose part. However, the contribution of the glucose-containing disaccharides other than maltose and sucrose to the availability of glucose in the Englyst method is zero. Breakdown of palatinose for instance only takes place in the intestines, involving the use of isomaltase. The aforementioned amounts of galactose and fructose according to the invention do not comprise the galactose-part of lactose and the fructose-part of sucrose and palatinose when used.

Also sugar polyols or sugar alcohols like isomalt, 6-O-α-D-glucopyranosyl-D-sorbitol or -mannitol, xylitol and/or sorbitol may beneficially be incorporated in the composition of the invention. When included the amount will typically be in the range of 2-14, preferably 4-10 wt % of the digestible carbohydrate fraction.

It is preferred that the sum of b1) carbohydrates capable of providing sustained release glucose, d) glucose-containing disaccharides other than maltose and sucrose, and, if present, e) sugar polyols is 35-65 wt % of the nutritional composition.

The composition preferably comprises the digestible carbohydrate fraction of the invention in an amount of 60-200, preferably 80-160, more preferably 10-140 g/l.

Where it is mentioned that the nutritional composition is heat-treated, it is meant that at least a liquid premix of the starch fraction is heat-treated, which subsequently can be mixed with the other components of the nutritional composition. However, the heat treatment can also be applied to the complete composition, in liquid form or to the carbohydrate fraction. In normal practices it appears possible to heat all components of the formula simultaneously and thus not only reducing the amount of micro-organisms to a sufficient degree, but also to treat the starch in a proper way to increase the amount of slowly digestible glucose moieties. In those cases where free amino acids or heat sensitive components like growth factors, immunoglobulins, reducing sugars, reactive ingredients or vitamins are present, the various fractions of the composition can be heat-treated differently.

A heat treatment makes it possible to prepare a liquid nutritional composition with low viscosity that can be applied for tube feeding as well as sip feeding, and wherein the starches are freely dispersible, resulting in favourable organoleptic properties.

Suitable heat treatment procedures include separate heating of fractions of the product in liquid form and aseptic blending of the appropriate amounts of each fraction, especially the protein and digestible carbohydrate fractions, the latter preferably combined with part of the lipid blend, in particular 1-30, preferably 2-10 wt % of the lipid blend to be included in the product, and optionally a vitamin fraction. Conventional heating practices can be applied, preferably a high-moist sterilization treatment. Suitable heat treatment procedures also include simultaneous heating of the complete product in case specific heat treatment practices are applied and protein sources are applied that comprise low amounts of sensitive lysine. Such specific heating practices include procedures that apply shorter heating times but still produce sterile products, like ultra high temperature treatment procedures (like UHT), that have been described as such in the art. Such products appear to provide sterile products that have experienced less Maillardation during processing.

Heat treatment procedures preferably involve heating of the composition for 0.1 seconds-6 minutes at a temperature at 100-180° C. They typically comprise one sterilization step and optionally one or more pasteurization or homogenization steps. More preferably, the heat treatment step includes heating at a temperature of 105-160° C., even more preferably 115-150° C. and in particular higher than 122° C. Although the preferred heat treatment time is between 0.1 seconds-6 minutes, the actual time is dependent on the heat treatment temperature. Typically the product will be heated for 2-6, preferably 3-5.5 minutes at 121° C., 12-36 seconds at 131° C., 1-4 seconds at 141° C. and 0.1-0.4 seconds at 151° C. Conditions at other temperatures can be interpolated and extrapolated from these numbers. The maximum amount of heating is not only determined by the amount of change in properties of the resistant starch, but also to the degree of Maillardation that may occur and the decomposition of heat sensitive products.

With standard knowledge regarding the amount of heating that is desired to kill micro-organisms to a sufficient degree, a decimal reduction of the total number of micro-organisms by at least a factor 3, preferably more than a factor 4 can be achieved. The success rate is dependent on the combination of temperature, heating time, degree of moisture, pressure and the presence of additional stressors like radiation or vibration, which are known to the person skilled in the art.

The heat-treated carbohydrate fraction and/or the heat-treated nutritional composition may be in the form of a free flowing powder or a concentrate comprising less than 5 wt %, preferably less than 1 wt % of water, based on the total weight. This can for instance be achieved by conventional spray drying after heat treatment.

In a preferred embodiment the nutritional composition is in the form of a liquid, suitable for tube or sip feeding. It has an osmolality of preferably 300-700, more preferably 330-600, most preferably 340-500 mOsm/l.

Preferably, the nutritional composition further comprises 10-30 wt %, based on the total dry weight of the carbohydrate fraction of groups a)-e) in the nutritional composition, of nutritional fibres. Such a carbohydrate fibre mixture preferably contains f) 40-55 wt % of non-digestible oligosaccharides, having a DP from 3 to 20, g) 40-55 wt % of non-digestible, non-soluble polysaccharides, and h) 0-20 wt % of non-digestible, soluble polysaccharides, the sum of f), g) and h) being 100 wt %.

In a preferred embodiment the fibre mixture contains 42-50 wt % of non-digestible oligosaccharides in group f), 42-50 wt % of non-digestible, non-soluble polysaccharides in group g), and 1-12 wt % of non-digestible, soluble polysaccharides in group h).

The polysaccharides of group g) preferably comprise 30-50 wt. %, based on the total fibre mixture, of resistant starch, i.e. the fraction of starch that remains undigested during the first 120 minutes of the Englyst test.

The non-digestible oligosaccharides of group f) preferably comprise 10-50 wt. %, based on the total fibre mixture, of galacto-oligosaccharides, especially β-galacto-oligosaccharides.

It is advantageous to include non-starch non-viscous fibres in the product. Viscous fibres, optionally in combination with other food components, are known to influence gastric emptying rates, and the rate of digestion of foods in the gastrointestinal tract. In addition, such fraction may provide a substrate for a healthy microbial flora in the gastrointestinal tract, and improve immune function in the target groups contemplated. It is now found that the fibres that preferably are included in the product according the invention should not behave as viscous fibres, both not in the product and neither in the gastrointestinal tract. The fibres of the invention are selected in such a way and included in such concentrations that they demonstrate a low viscosity in a nutritional composition. These fibres appear to demonstrate a low viscosity also under in vivo conditions. Fibres that can be used in the invention are trans-galacto-oligosaccharides (GOS), and extensively hydrolysed gums, hydrolysed mannans, hydrolysed arabans, hydrolysed xylans, hydrolysed beta-glucans, hydrolysed fructans (fructose-oligosaccharides, FOS), inulin and/or oligofructoses.

The total amount of non-starch and starch fibres, including the NDS fraction of the resistant starch ingredient, can be in the range of 2-30, preferably 3-18, more preferably 4-14 and most preferably 5-12 g/l. The viscosity of the product is low in order to provide acceptable flowing characteristics for sip-drinking and for tube feeding. Measured at 20 degrees Celsius at a shear rate of 100/sec, viscosity must be 1-60, preferably 1.4-40, more preferably 1.8-30 Mpa·s (for reference: the value for water is one).

The nutritional composition preferably contains a carbohydrate mixture comprising the aforementioned fibre mixture, together with a high-amylose digestible glucose source, the weight ratio between the fibre mixture and the high-amylose glucose between 2:1 and 1:5. With a "high-amylose digestible glucose source" comprise it is understood a glucose source which is digestible within 120 minutes according to the Englyst test, and which contains more than 50% amylose of its total content.

The invention also pertains to a carbohydrate mixture comprising the fibre mixture according to any one of the preceding claims, and a low glycemic component of one or more of the following:

α): one or more monosaccharides selected from galactose, ribose and mannose;

β): glucose-containing disaccharides other than maltose and sucrose;

γ): fructose and/or sucrose; and

δ): sugar polyols, wherein the weight ratio between the fibre mixture and the low glycemic component is between 2:1 and 1:10, and to the use of such a composition for controlling glucose levels in blood and/or tissue in a mammal in need thereof.

The carbohydrate mixture preferably comprises 40-120 wt %, based on the weight of the fibre mixture, of (α) one or more monosaccharides selected from galactose, ribose and mannose.

The compositions of the invention may further comprise an insulin-releasing agent, preferably sulfonylurea, and/or an antidiabetic drug, preferably biguanidine and/or thiazolidinedione. If sulfonylurea is present, the composition of the invention preferably contains an amount of 0.1-4 g per kg thereof.

The nutritional compositions further comprise a protein fraction. Such a protein fraction is based on a source of vegetable protein, to which at least one free amino acid, a peptide or a protein from animal source is added. The vegetable protein can be selected from soy, pea, lupine, potato, beans, sunflower, rape seed, etc. The amino acids or peptides are selected to be rich in those amino acids which increase nutritional value of the protein fraction as a whole in terms of the demand for essential amino acids. In particular these amino acids are lysine, leucine, and phenylalanine. The protein source of animal origin is selected in particular from milk proteins and liquefied proteins from muscle from animal or fish, like hydrolysed proteins. Milk proteins are particularly preferred, especially whey proteins and more in particular those whey proteins that comprise less than 40 wt % and preferably less than 30 wt % kappa-casein or glycomacropeptide, calculated on protein base.

The amount of protein in the compositions is preferably 0.5-20 g, more preferably 1-8 and most preferably 2-7 g per 100 ml product. Calculated as the amount of energy that is provided by proteins, lipids and digestible carbohydrates, by using the Atwater factors (4, 9, 4) for each of them, the amount of energy for protein is 10-30, preferably 14-28, most preferably 17-26 en %, for lipids 25-45, preferably 28-40 and most preferably 30-38 en % and for digestible carbohydrates 35-70, preferably 40-60 and most preferably 42-55 en %. The composition comprises 5-80, preferably 20-50 g/l of a protein fraction.

The compositions may comprise per 100 g amino acids 1.8-5 g methionine, and/or 4.5-9 g threonine, and/or 8.6-17 g leucine, and/or 5.5-9.5 g proline. The protein fraction preferably originates for 15-99.9 wt %, preferably 20-95 wt % from plant species belonging to the species of fabales or leguminosae.

It is preferred that the proteins originate from one or more members of the group of soybean (*Glycine max*), pea (*Pisum* species), bean (*Phaseolus* species), fenugreek (*Trigonella* species), lupine, lentil (*Lens* species), peanut (*Arachis* species), tamarind, clover and alfalfa.

Such protein compositions further support the improvement of postprandial glucose response and postprandial insulin response. They appear not to impart the amount of rapidly available glucose, however further decrease maximum glucose levels and elongate glucose supply of the product.

Other organoleptic properties like taste and smell can be influenced by applying methods known in the art, using odorants and taste modifiers as required. Consistency and mouth feel depend on particle size of the ingredients and degree of homogenizing. Apart from the particle size for the sustained glucose source as discussed above also the other ingredients should not comprise large particles. In particular the minerals should not sediment. In order to achieve this, only soluble forms of divalent ions like calcium, zinc and magnesium were used during manufacture. Such forms are known in the art and include complexes and compounds with organic counter ions. The amount of calcium and phosphorous are also selected to be within the range of 10-70, preferably 20-60 mg/100 ml. The ratio of calcium to phosphorous is in the range 0.8-2, preferably 1.1-1.9, more preferably 1.3-1.8.

The compositions of the invention further comprise a fat or lipid fraction. Such a lipid fraction comprises oleic acid and essential fatty acids like linoleic acid and α-linolenic acid, but could also comprise conjugated linolenic acids and omega-3 long-chain fatty acids like eicosapentaenoic acid and docosahexaenoic acid. The fatty acids comprise less than 10 wt % saturated fatty acids, and less than 2, preferably less than 1 wt % of trans fatty acids. The amount of lipid is 10-60, preferably 15-50, more preferably 31-46 g/l. Expressing the amount of lipid in the product as en % using the Atwater factors the amount of lipid is 25-45, preferably 28-40 and most preferably 30-38 en %. Lipids are contemplated to include triglycerides or triacylglycerides, di-glycerides or diacylglycerides, monoglycerides or monoacylglycerides, phospholipids, lysophospholipids, sphingolipids, and ceramides Other components that are soluble in petroleum ether or hexane, like cholesterol and other sterols, are not included in calculations about the lipid fraction.

Moreover the product can comprise micro-ingredients like vitamins, trace elements and minerals that are known in the art and carnitine equivalents, inositol, taurine and other food constituents such as flavours, colorants or manufacturing aids.

The carbohydrate fraction and nutritional composition according to the invention are useful in maintaining a low and prolonged glucose response in blood and tissue after consumption, and especially useful in cases of diabetics and/or insulin-resistance. People that suffer from or are extremely susceptible to insulin-resistance are e.g. severely or critically ill patients, in particular palliative patients like those that suffer from severe cancer or HIV infection. Other groups of patients suffering from difficulties to control their PPGR comprise those persons that were subjected to major surgery or exposed to other traumata, malnourished persons in particular those suffering from protein-energy malnutrition, persons that suffer from obesity, the Metabolic Syndrome, Syndrome X, hyperglycemia, hyperinsulinemia, dyslipidemia hypertriglyceridemia and dysfibrinolysis, but also large parts of the group of the elderly in Western societies. In addition the product can be useful for persons that have an increased risk in terms of a hereditary history of developing insulin resistance, obesity or diabetics like many Hindustan persons and several Caucasian families, for persons that plan irregular feeding pattern, like sportsmen during an enduring exercise or persons that desire to maintain attention for longer periods of time, like students during studying or examines or during meetings.

It is thus an object of the invention to use the nutritional compositions according to the invention for the prevention and/or treatment of diabetics, insulin-resistance, obesity, controlling postprandial glucose response, metabolic syndrome, syndrome X, hyperglycemia, hyperinsulinemia, dyslipidemia, hypertriglyceridemia, dysfibrinolysis and/or disorders associated with major surgery or trauma in a mammal, by maintaining a substantially stable glucose level or PPGR in the mammal's blood for a period starting after 20 minutes to 4 hours after administration. It is even more preferred to maintain the glucose concentration stable until 3 hours, more preferably until 2 hours after administration.

With "substantially stable" glucose level or PPGR it is understood that the glucose level in blood does not vary more than about 1.6 mM and preferably less than 1.3, more preferably less than 1.0 mM per 20 minutes during the abovementioned period after consumption.

In case of diabetics, the glucose blood levels are typically maintained between 4 mM and 15 mM. However, in the case of severe diabetics peak postprandial glucose concentrations above 15 mM can still be observed. Under these circumstances the nutritional composition comprising the carbohydrate fraction of the invention should be consumed in more than one eating session and/or in combination with administration of an appropriate amount of insulin prior to consumption of the food product. In case of non-diabetics it is possible to control the glucose blood level even below 11 mM.

Preferably the glucose levels in plasma can be controlled between 5 and 8 mM in the abovementioned period, without the necessity to consume large amounts of fibre with it, as this may cause gastrointestinal discomfort, and without replacing glucose sources by other carbohydrates, which demand an unrealistic high metabolic capacity in the person, or by high amounts of lipids, which may disturb physiologically acceptable blood lipid or cholesterol profiles.

Moreover the product is effective in decreasing the risk for obtaining and decreasing the aggravation of several diseases which are associated with frequently elevated blood glucose levels, which include retinopathies, kidney diseases and neuropathies. Also diseases associated with the occurrence of advanced glycation products (AGE) can be prevented. Effectivity of the product can be determined by measuring the levels of glycated haemoglobin molecules (Hb1Ac) in blood.

EXPERIMENTAL

Experiment I

Healthy male Wistar rats (n=9, weighing 225-250 g at arrival) were kept in a temperature- and light-controlled room (dark period: 16:00 h-4:00 h), with ad libitum access to food (Teklad standard lab chow) and tap water unless otherwise stated. Under isoflurane anaesthesia, the rats received a permanent intragastric canula in order to allow frequent and stress-free intragastric administration of compounds, and a permanent canula in the right atrium in order to allow frequent and stress-free blood sampling. On the day of the experiment, food was removed at 8:30 h. At 13:30 h, the rats received a bolus of 2.0 g carbohydrate/kg dissolved in water.

Administered volumes (approximately 6 ml) were corrected for the body weight of each individual rat and the carbohydrates were corrected for digestibility. At 10 minutes before and 5, 10, 15, 20, 30, 45 and 75 minutes after administration of the bolus, blood samples were taken and collected in ice-chilled, heparinised tubes. In each rat, 4 different, randomly assigned or carbohydrate sources were tested. At least one week of recovery was allowed between 2 subsequent experiments.

Figure 1:
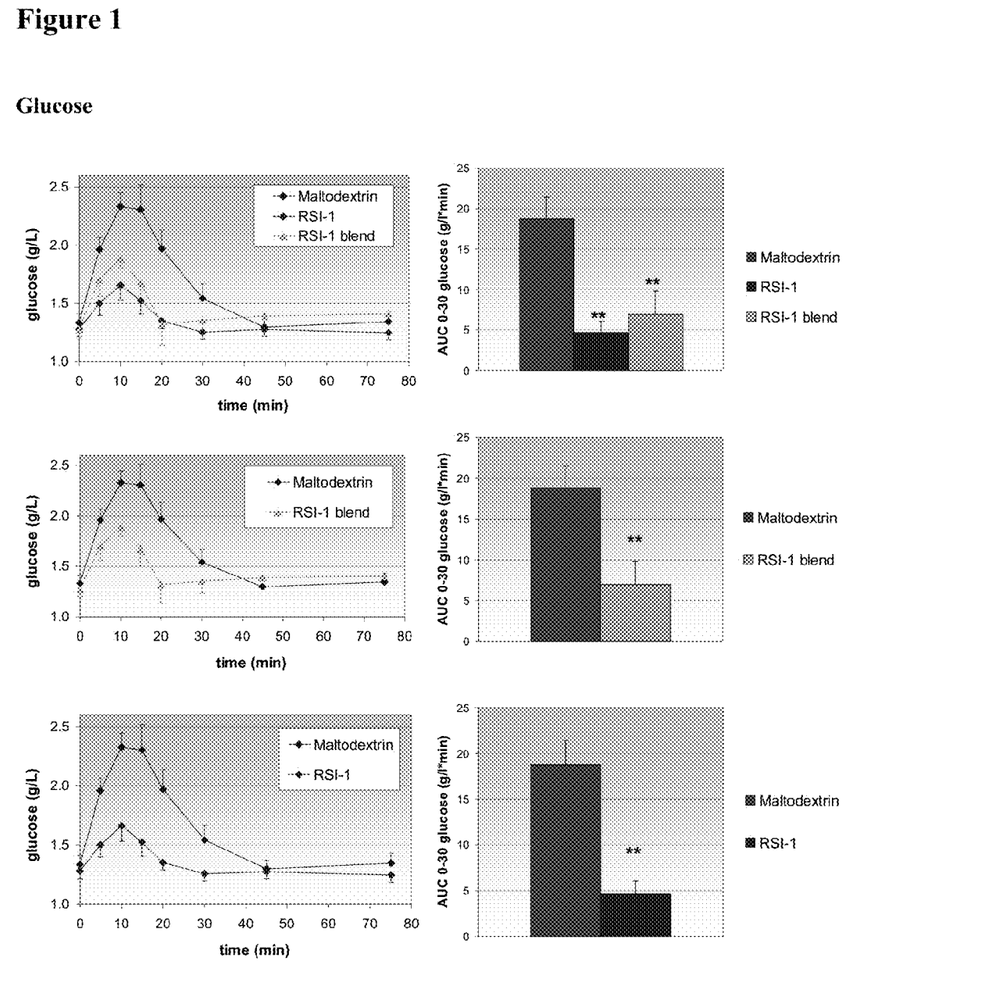
FIG. 1 shows postprandial glucose response in rats following consumption of a resistant starch ingredient according to the invention ("RSI-1"), consumption of a resistant starch ingredient according to the invention with other digestible carbohydrates ("RSI-1 blend"), or conventional maltodextrins.
Figure 2:
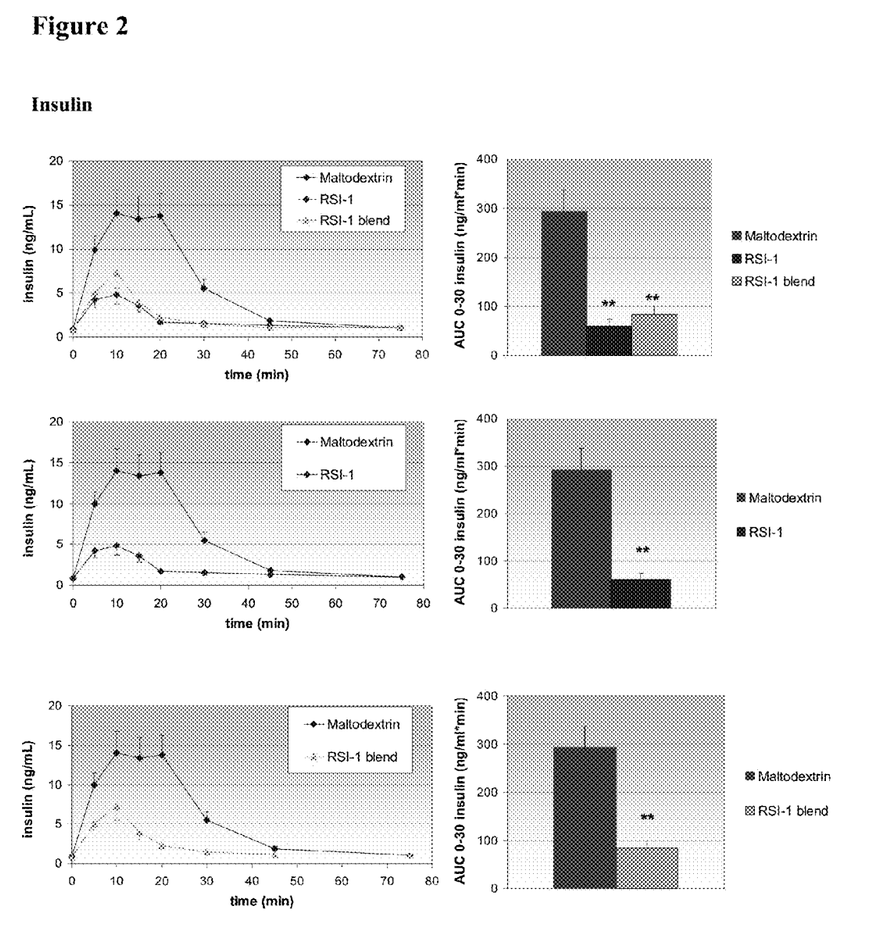
FIG. 2 shows insulin response in rats following consumption of a resistant starch ingredient according to the invention ("RSI-1"), consumption of a resistant starch ingredient according to the invention with other digestible carbohydrates ("RSI-1 blend"), or conventional maltodextrins.

Results:

The figures demonstrate that the PPGR after consumption of the resistant starch ingredient according the invention (RSI-1; having RDS: 40%, SDS 35%, NDS 25% according to the Englyst method) is much better than after consumption of conventionally used maltodextrins, both in terms of quick availability of glucose as in a sustained provision of glucose moieties, e.g. 45 minutes after consumption of the carbohydrate mix. This PPGR is further improved after blending the ingredient with the other digestible carbohydrate components. Also insulin release was improved.

Experiment 2

Figure 3:
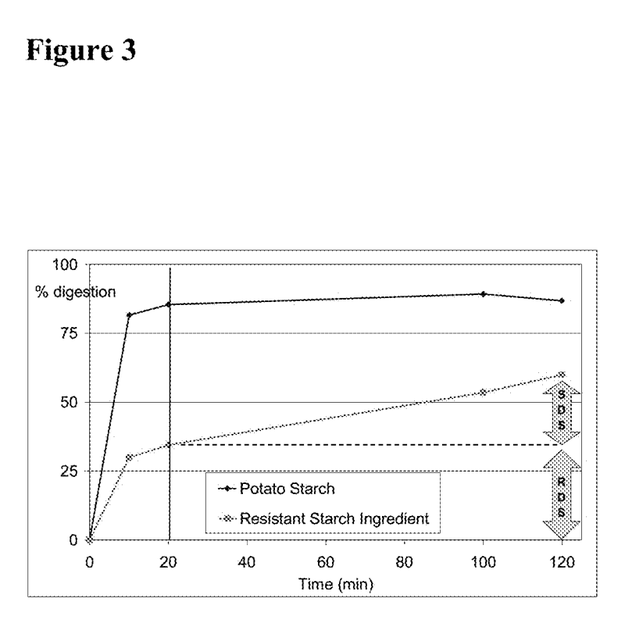
FIG. 3 shows the glucose release pattern of potato starch and heat treated resistant starch ingredient.

The glucose release pattern of potato starch and heat treated resistant starch ingredient were tested by applying the method as described by Englyst 1999 as specified in the description. These ingredients appeared to release significantly different amounts of glucose between 0-20 minutes (RDS fraction) and 20-120 minutes (SDS fraction) after start of the test. The results are plotted in the figure below.

EXAMPLES

---

1. Method for measuring amylose content.

The carbohydrate is dissolved in dimethylsulfoxide and 20 µl is injected on a Shodex KS804 column. MilliQ water is used as eluting solvent to separate all components. A Shimadzu RID-10A is used as detector and poly α-1-4-Glc-Glc standards were used for calculation purposes. Those components of the material that elute after the standards that have a degree of polymerization of 20 or more are called amyloses.

2. Carbohydrate blends suitable for use in complete nutritional products (amounts are given as gram per 100 g of digestible blend).

| | | |
|---|---|---|
| galactose | 20 | |
| glucose | 15 | |
| resistant starch ingredient | 62 | (of which 50 is digestible) |
| hydrolysed starch | 15 | |

-continued

| 3. Carbohydrate blend | | |
|---|---|---|
| ribose | 15 | |
| hydrolysed starch | 40 | |
| resistant starch ingredient | 58 | (of which 35 is digestible) |
| sucromalt (60% oligoglucose, 40% fructose) | 10 | |

| 4. Carbohydrate blend | | |
|---|---|---|
| galactose | 20 | |
| lactose | 15 | |
| isomalt | 10 | |
| resistant starch ingredient | 75 | (of which 40 is digestible) |
| hydrolysed starch | 15 | |

| 5. Carbohydrate blend | | |
|---|---|---|
| galactose | 10 | |
| mannose | 10 | |
| glucose syrup | 15 | |
| resistant starch ingredient | 55 | (of which 35 is digestible) |
| isomaltose | 10 | |
| palatinose | 20 | |

| 6. Carbohydrate blend | | |
|---|---|---|
| ribose | 15 | |
| mannose | 5 | |
| glucose syrup | 20 | |
| resistant starch ingredient | 65 | (of which 30 is digestible) |
| lactose | 10 | |
| isomalto-oligosaccharides | 20 | |

| 7. Liquid formula for diabetics | | |
|---|---|---|
| Energy content | 0.7-1.3 kcal/ml | |
| Protein: | 17-26 en % | Soy protein isolate/α-lactalbumin-enriched whey (50/50) |
| Lipids: | 30-38 en % | |
| Carbohydrates | 42-55 en % | Any of the blends as described in examples 1-6 |
| Fiber | 1 g/100 ml | |
| Minerals, trace elements and vitamins according to the recommendations of US Food and Drug Administration. | | |

8. Liquid product for diabetics type II. Amounts per 100 ml

| | | |
|---|---|---|
| Energy | 1.0 kcal/ml | |
| Protein | 4.8 g | Lupine 1.5 |
| | | Fenugreek 0.25 |
| | | Milk protein 3.0 |
| Lipids | 4.0 g | Saturated 0.34 |
| | | MUFA: 2.5 |
| | | PUFA: 1.2 (EPA 0.2) |
| Carbohydrate | 11.00 g | Galactose 2 |
| | | Glucose 2 |
| | | Isomalt 1 |
| | | Tapioca starch 1.9 |
| Resistant starch ingredient | 5.4 g | (of which 4.1 digestible) |
| Fibre | 2 g | Resistant starch 1.3 |
| | | Galacto-oligosaccharides 0.7 |

9. Bar for use by persons expecting irregular eating patterns or for inter-meal feeding (e.g. diabetics before bedtime) and to prevent hypoglycemia. Amounts per 100 g dry mass.

| | | |
|---|---|---|
| Protein: | 19 g | |
| Pea protein + α-lactalbumin enriched whey + L-methionine (60:39:1) | | |
| Carbohydrates: | 57 g | |
| Resistant starch ingredient, glucose syrup, galactose, glucose (50:30:10:10) | | |
| Lipids: | 18 g | |
| Fibre: | 4 g | |
| Minerals/vitamins/trace elements/aids: | 2 g | |

10. Liquid formula for enteral use by critically ill

| | | |
|---|---|---|
| Energy | 1.25 kcal/ml | |
| Protein | 7.5 g | casein 3.1 |
| | | glutamine 1.3 |
| | | arginine 0.9 |
| Carbohydrates | 14.5 g | galactose 2 |
| | | glucose 2 |
| | | resistant starch ingredient 8 |
| | | maltodextrins 2.5 |

| | | -continued |
|---|---|---|
| Lipids | 4.2 g | saturated 2.1 (of which 1.7 is MCT oil)<br>MUFA 0.7<br>PUFA 1.4 |
| Dietary fibre | 0.9 g | |

The invention claimed is:

1. A heat-treated liquid nutritional composition comprising lipids, proteins and digestible carbohydrates, wherein the digestible carbohydrates in said composition comprise:
 a: 5-30 wt. % galactose;
 b: carbohydrates capable of providing b(1) sustained-release glucose and b(2) rapidly available glucose;
 c: optionally fructose, wherein the amount of fructose is 0-10 wt. %;
 d: optionally glucose-containing disaccharides other than maltose and sucrose, wherein the amount of glucose-containing disaccharides other than maltose and sucrose is 0-30 wt. %; and
 e: optionally sugar polyols, wherein the amount of sugar polyols is 0-14 wt. %,
 wherein the percentages are based on the dry weight of the sum of groups a-e in the heat-treated liquid nutritional composition, said composition comprising 0.5-10 wt. % heat-treated resistant starch comprising 8-55% of non-digestible starch (NDS), 35-50% of slowly digestible starch (SDS) and 20-50% of readily digestible starch (RDS), the total of NDS, SDS and RDS being 100%.

2. The nutritional composition according to claim 1, wherein group b) provides 5-65 wt % of carbohydrates capable of providing sustained-release glucose.

3. The nutritional composition according to claim 1, wherein group b) provides 5-40 wt % of rapidly available glucose.

4. The nutritional composition according to claim 1, wherein group d) is present in an amount of 5-30 wt %.

5. The nutritional composition according to claim 1, wherein group e) is present in an amount of 2-14 wt %.

6. The nutritional composition according to claim 1, wherein the sum of b) and d) and e) is 35-65 wt %.

7. The nutritional composition according to claim 1, wherein group c) is present in an amount of 1-10 wt %.

8. The nutritional composition according to claim 1 further comprising 10-30 wt %, based on the total dry weight of the digestible carbohydrate fraction of groups a)-e) in the nutritional composition, of nutritional fibres.

9. The nutritional composition according to claim 8, wherein said nutritional fibres further comprise:
 f. 40-55 wt % of non-digestible oligosaccharides, having a DP from 3 to 20;
 g. 40-55 wt % of non-digestible, non-soluble polysaccharides; and
 h. 0-20 wt % of non-digestible, soluble polysaccharides.

10. The nutritional composition according to claim 8, wherein said nutritional fibres further comprise:
 f. 42-50 wt % of non-digestible oligosaccharides;
 g. 42-50 wt % of non-digestible, non-soluble polysaccharides; and
 h. 1-12 wt % of non-digestible, soluble polysaccharides.

11. The nutritional composition according to claim 9, wherein said polysaccharides of group g) comprise 30-50 wt. %, based on the total fibres, of resistant starch.

12. The nutritional composition according to claim 9, wherein said non-digestible oligosaccharides of group f) comprise 10-50 wt. %, based on the total fibre mixture, of galacto-oligosaccharides.

13. The nutritional composition according to claim 8, wherein said composition further comprises a high-amylose digestible glucose source, the weight ratio between the nutritional fibres and the high-amylose glucose between 2:1 and 1:5.

14. The nutritional composition according to claim 8, wherein the weight ratio between the nutritional fibres and the sum of the low glycemic components a), c), d) and e) is between 2:1 and 1:10.

15. The nutritional composition according to claim 8, wherein said digestible carbohydrate fraction comprises 40-120 wt %, based on the weight of the nutritional fibres, of (a) one or more monosaccharides selected from galactose, ribose and mannose.

16. The nutritional composition according to claim 1, wherein the weight ratio of the amount of rapidly available glucose to group a) is 1.25-10:1.

17. The nutritional composition according to claim 3, wherein group b) provides 15-40 wt. % of rapidly available glucose.

18. The nutritional composition according to claim 4, wherein group d) is present in an amount of 5-20 wt %.

* * * * *